United States Patent [19]

Cohen

[11] Patent Number: 4,484,933
[45] Date of Patent: Nov. 27, 1984

[54] PROCESS FOR DRYING GAS STREAMS

[75] Inventor: Alan P. Cohen, Houston, Tex.

[73] Assignee: Union Carbide Corporation, Danbury, Conn.

[21] Appl. No.: 504,148

[22] Filed: Jun. 14, 1983

[51] Int. Cl.³ .............................................. B01D 53/04
[52] U.S. Cl. .......................................... 55/25; 55/33; 55/35; 55/68; 55/75
[58] Field of Search .................. 55/25, 31, 33, 35, 58, 55/62, 68, 75

[56] References Cited

U.S. PATENT DOCUMENTS

| | | | |
|---|---|---|---|
| 2,570,974 | 10/1951 | Neuhart | 55/31 X |
| 2,966,531 | 12/1960 | Louis | 55/75 X |
| 3,078,636 | 2/1963 | Milton | 55/75 X |
| 3,078,637 | 2/1963 | Milton | 55/75 X |
| 3,216,178 | 11/1965 | Sauty | 55/33 |
| 3,238,701 | 3/1966 | Holt | 55/33 X |
| 3,712,027 | 1/1973 | Hasz | 55/33 |
| 3,713,272 | 1/1973 | Barrere, Jr. et al. | 55/33 |
| 3,728,844 | 4/1973 | Snyder et al. | 55/33 |
| 3,756,961 | 9/1973 | Francis et al. | 55/33 X |
| 3,766,660 | 10/1973 | Settlemyer | 55/31 X |

Primary Examiner—Robert Spitzer
Attorney, Agent, or Firm—Richard G. Miller

[57] ABSTRACT

The integration of a single auxillary fixed adsorption bed into a system comprising at least two principal treater beds for the adsorption-purification of gas streams containing water vapor results in reduced capital investment and purge gas requirements. During purge desorption of a principal treater bed the effluent is recycled through a closed loop containing the auxillary bed. Regeneration of the auxillary bed is accomplished at least in part using the effluent from the treater bed during cooldown.

4 Claims, 1 Drawing Figure

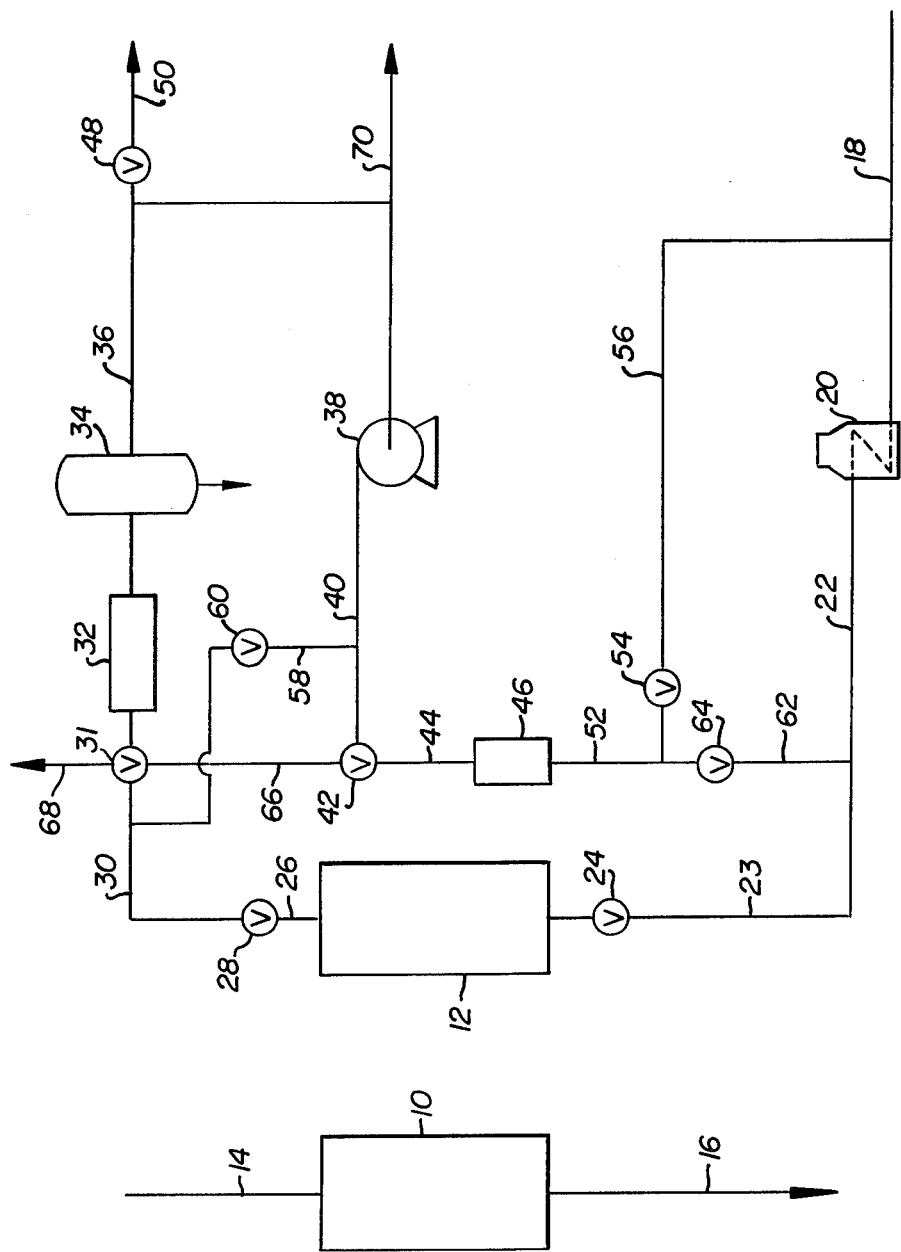

PROCESS FOR DRYING GAS STREAMS

The present invention relates in general to reducing the water vapor content of gaseous feedstocks and more particularly to the gas phase dehydration of hydrocarbon feedstocks by the selective adsorption of the water content thereof using fixed beds of zeolitic molecular sieves.

A large number of gaseous materials which ultimately are subjected to various physical and/or chemical treatments are produced or found in nature in admixture with significant quantities of water vapor. These include natural gas (methane) and propane which in some instances are liquified prior to being transported or stored; carbon dioxide which is solidified for use as a refrigerant; hydrogen to be utilized in various catalyzed hydrocarbon conversion reactions; thermally cracked hydrocarbons to be liquified and fractionated to recover individual product species such as olefins; and ethylene as a feedstock for a polymerization or oligomerization. It is a common means for purifying such gaseous feedstocks to remove water vapor (and also other contaminants such as $H_2S$ and $CO_2$) by selectively adsorbing the species of smaller molecular dimensions or greater polarity on zeolitic molecular sieve adsorbents. Usually one or more fixed beds of the zeolite adsorbent is employed, with each bed undergoing the cyclic steps of (a) adsorption (b) hot purge regeneration and (c) cooling.

Since water has a very strong affinity for zeolitic molecular sieves, particularly those in which the $SiO_2/Al_2O_3$ molar ratio of the crystal framework is less than about 20, it is desorbed with considerable difficulty. Practical considerations of time and expense very often dictate that regeneration of a bed loaded with adsorbed water involves raising the temperature of the bed considerably above the temperature at which the water was initially adsorbed during the purification of the feedstock. Because the adsorbent particles are not very effective heat conductors, heating of the bed is almost invariably accomplished by heating the purge gas introduced into the bed during the regeneration procedure, thereby causing the purge gas to serve the dual function of heating the adsorbent to lessen its affinity for the adsorbate and purge the desorbed water molecules from the intracrystalline void spaces as well as the void space of the bed. Moreover, when the regeneration is complete, the bed must be cooled back to the temperature suitable for adsorption of water from additional feedstock fed to the bed on the succeeding adsorption-purification stage. Here again a cooled purge gas relied upon to transfer the excess heat from the bed in the reverse of the heating procedure.

Thus in most separations of the type mentioned above, there is a considerable requirement for purge gas and heat energy. There is, moreover, a direct correlation between the moisture content of the purge gas stream used in purge desorption and cool-down operations and the moisture content of the purified product. This is due to the near equilibrium established between the adsorbed water on the adsorbent and the water in the purge gas phase over the adsorbent. The level loading of water vapor throughout the adsorbent bed determines the water content of the product gas stream since an equilibrium is also established between the product stream moving through the bed and the adsorbent mass during the adsorption-purification stage.

It is commonly the case, therefore, that the desired degree of dryness of the product requires the use of a purge gas stream having a very low water content. Only rarely are such gas streams which are suitable both from the standpoint of dryness and quantity available at the site of the intended purification operation. It is not surprising, therefore, that much attention has been given to the conservation of purge gas and the recovery of heat energy in adsorption-purification processes. Many ingenious combinations of process apparatus and flow schemes have been devised which take advantage of the peculiar aspects of particular feedstocks and the uses to which the purified product will be put. Often a portion of purified product gas, such as natural gas, can be used for regeneration purposes and the highly impure effluent from the regenerating bed used as a fuel gas for supplying heat to the process involved, or in other non-related processes elsewhere in the same vicinity. In many instances, however, the principal ingredient of the feedstock is too valuable to be wasted in any significant degree as a purge gas, or the degree of purity required for the product is too high to permit less than thorough regeneration of the adsorption bed.

An alternative is the integration of an auxilliary drying system into the principal purification process system so that a purge gas which is available in sufficient quantity but having too high a water content can be pre-dried before use in the principal process system. For this purpose it has been proposed to utilize an auxilliary two-bed molecular sieve adsorbent system so that the dry purge gas produced is available on a continuous basis for use in the principal process, the latter also being operated on a continuous basis using a plurality of adsorbent beds. Although this is a satisfactory solution to the problem insofar as achieving the desired results is concerned, the capital and operating costs are significant disadvantages. It has now been discovered that in a process for drying gas streams in which at least two primary (treater) molecular sieve adsorption beds are employed, it is possible not only to substantially decrease the capital investment and operating costs attendant the use of a two-bed auxilliary purge gas drying system, but also substantially to reduce the quantity of purge gas and, in certain instances, the heat energy required to regenerate the beds. In this novel process, only a single auxilliary molecular sieve bed is incorporated into the system and used for the purpose of purifying the purge gas stream as it is recycled through a primary bed during the regeneration procedure. The auxilliary bed is itself regenerated, either entirely or in substantial part, using the heat energy stored in the primary bed at the beginning of the primary bed cool-down. The dry hot effluent, or a portion thereof, from the primary bed during cool-down is passed through the auxilliary bed so that purge gas involved performs two functions. In its generic sense the present invention can be stated as follows: In the process for drying a feedstock gas stream containing at least 1.0 ppm water vapor wherein the gas stream is passed through a first primary fixed adsorbent bed of zeolitic molecular sieves to selectively adsorb the water vapor and recover an effluent gas stream of reduced water content, periodically diverting the feedstock gas stream to a second primary fixed adsorption bed containing regenerated molecular sieve adsorbent wherein adsorptive drying of the feedstock is continued and the first primary adsorption bed is purge desorbed using a heated non-sorbable purge gas stream and thereafter cooled in preparation for having the feedstock gas stream diverted thereinto for the drying of an additional portion thereof, the improvement which comprises cyclically passing the heated non-sorbable purge gas stream through the first primary adsorption bed in a direction counter-current to the direction of flow of the feedstock gas stream therethrough and subjecting the effluent from said bed to the sequence of treatments comprising (a) decreasing the temperature of said effluent at least 75° C., and preferably at least 200° C.;

(b) passing the cooled gas phase through an auxilliary fixed bed containing activated zeolitic molecular sieve whereby essentially all of the water vapor present therein is adsorbed; and (c) heating the effluent gas stream from said auxilliary fixed bed to the temperature desired for regeneration of the first primary fixed adsorption bed, and passing the heated gas stream into the first primary fixed bed to complete the cycle;

continuing the aforesaid cyclic purge desorption until the desired degree of bed regeneration is accomplished and thereafter cooling the first primary fixed adsorption bed and simultaneously at least partially, and preferably fully, regenerating the auxilliary fixed bed by passing a cool non-sorbable gas stream through the first primary fixed bed in a direction counter-current to the direction of cyclic flow of heated purge gas therethrough and passing the heated effluent therefrom, or a portion thereof, through the auxilliary fixed bed, the quantity of said cool non-sorbable purge gas being sufficient to cool the first primary fixed bed to the desired temperature for a subsequent resumption of adsorption-drying of feedstock gas stream therein. In those cases where the recoverable heat energy from the cooling primary bed is not sufficient to completely regenerate the auxilliary bed, additional heat energy can be supplied by passing at least a portion of the non-sorbable purge gas stream through a heater before it is passed through the auxilliary bed.

The vapor phase feedstocks treated in accordance with the present invention are not narrowly critical with respect to composition, and include any compound or mixture of compounds which are either the so-called permanent gases or which are in the gas phase under the temperature and pressure conditions suitable for the adsorption-separation process, which are not reactive inter-se or with the zeolitic adsorbent mass employed under the imposed conditions, which contain from 1 to 1500 ppm (v) of water vapor, and which are less strongly adsorbed than water on molecular sieve zeolites. Preferably the feedstocks are primarily hydrocarbons which in addition to water vapor can contain minor proportions of impurities such as CO, $CO_2$, $H_2S$, mercaptans and the like which are commonly encountered in feedstocks derived from petroleum refining or the conversion of coal, alcohols and synthesis gas to liquid and gaseous hydrocarbons. The process is readily adaptable to the removal of one or more of these impurities along with the water impurity, or if desired, only the water is removed. Particularly preferred feedstocks are olefinic materials such as ethylene and propylene.

The molecular sieve adsorbent employed can be any crystalline microporous solid having an open framework structure of tetrahedral metal oxides, particularly $PO_2$, $AlO_2$ and $SiO_2$ tetrahedra, uniform pores having nominal diameters large enough to permit passage of water molecules and a capacity for selectively adsorbing water under the imposed conditions in an amount of at least 4 weight-%. These molecular sieves include the well-known zeolite molecular sieve which is composed essentially of $AlO_2$ and $SiO_2$ tetrahedra, and also the more recently discovered aluminophosphate molecular sieves in which the crystal framework is composed of $PO_2$ and $AlO_2$ tetrahedra. Other molecular sieve materials in which other tetrahedral oxide species are substituted for the $PO_2$, $AlO_2$ or $SiO_2$ tetrahedra in the crystal structure are also suitably employed. Of the zeolitic molecular sieves, zeolite A and zeolite X are particularly employed because of their large capacity for adsorbing water and their relatively low cost. Suitable aluminophosphate molecular sieves are disclosed in U.S. Pat. No. 4,310,440 issued Jan. 12, 1982 and incorporated herein by reference.

The temperature and pressure conditions in the adsorption beds and elsewhere in the adsorption system are those generally found to be suitable in other adsorption-purification process schemes, taking into account the nature of the feedstock. During the adsorption stroke when feedstock is being passed through a primary adsorber to selectively adsorb and remove water, and optionally other impurities, the temperature of the feedstock is generally kept below about 65° C. in order to maximize the degree of water loading. Also pressure within the adsorber will preferably be at least one atmosphere and can advantageously be higher when the water partial pressure of the feedstock is low, in order to increase the water vapor pressure over the adsorbent and increase the resulting water loading. The degree of increase in pressure above one atmosphere and the temperature conditions are controlled with respect to each other and with reference to the feedstock to maintain vapor phase operation with optimum efficacy in the manner well known in the art.

During the regeneration of a primary adsorbent bed the purge gas is heated to temperatures significantly higher than the temperature of the adsorbent mass in order to lower the equilibrium water loading and facilitate desorption and purging of the water (and other impurity adsorbates) from the bed. In general the higher the purge gas temperature, the less the quantity of purge gas required, although such factors as hydrothermal abuse of the adsorbent and higher heat energy losses due to untoward differentials between internal and external bed temperatures will be taken into account by those skilled in the art. It is not necessary that the purge gas be heated over the entire period of the hot purge regeneration, since the heat of the regenerated adsorbent mass at the ingress end of the bed during regeneration can be carried forward even with unheated incoming purge gas, but the primary bed at the end of the regeneration stage will advantageously contain sufficient heat energy so that upon the following cool-down purge, the effluent purge gas is capable of regenerating the auxilliary adsorbent bed. Factors which determine the accomplishment of this result include the relative sizes of the primary and auxilliary beds and the water loading of the auxilliary bed. Routine calculations are readily made in view of any given process system to establish suitable process conditions.

The non-adsorbable purge gas employed can be any of those commonly used in other adsorption-separation processes and include hydrogen, nitrogen, helium, argon and the other inert gases and methane. It will be understood that the term "non-sorbable purge gas" is used in its relative sense and includes materials which have some degree of affinity for molecular sieves but which are easily displaced from the adsorbent by water and any other impurity of the feedstock which is desired to be removed along with the water, and which is not an undesired component of the product gas stream.

The process of the present invention is illustrated by the following description with reference to the drawings.

IN THE DRAWINGS

FIG. 1 is a flow diagram illustrating the operation of two embodiments of the present process wherein regeneration of the auxilliary drying bed is accomplished in part by displacement of some of the adsorbed water therefrom to the ingress end of a primary drying bed, and wherein regeneration of the auxilliary drying bed is accomplished without displacing any water desorbed therefrom to a primary drying bed.

In actual practice both beds, i.e., beds 10 and 12 in FIG. 1 would be integrated into the overall system so that with appropriate valving and piping the feedstock being treated and the purge gas streams used to regenerate and cool the beds can be passed through the beds in the proper direction and at the proper time in order that operation is continuous. Details of the construction of an actual system are well within the routine skill of the art, and tend to obscure the true nature of the present invention if included in the drawings. Accordingly the flow scheme of FIG. 1 contain only the conduits, valves, etc., which are essential to the illustration of the embodiments concerned.

With reference to FIG. 1, primary adsorption beds 10 and 12 each contains 7000 lbs. of type NaX molecular sieve zeolite pellets, and auxilliary bed 46 contains 600 lbs. of type KA molecular sieve zeolite pellets. A feedstock consisting of ethylene, 2 ppm carbon dioxide and 20 ppm (vol.) water vapor is fed through line 14 at a temperature of 73° F. into bed 10 which is at a temperature of 73° F. The water component of the feedstock is selectively adsorbed at the ingress end of the bed and forms a water adsorption front which, with increasing adsorption of water from the incoming feedstock, advances downward through the bed. The ethylene passes through the bed and is recovered as the purified product through line 16. At the beginning of the adsorption stroke in bed 10, the same type of adsorption stroke had just been completed in bed 12 with the result that water adsorption front has been moved toward the egress end of bed 12 and the adsorbent particles above the front contained a loading of adsorbed water. Accordingly regeneration of bed 12 is carried out over the period when bed 10 is being used to treat feedstock. Regeneration of bed 12 is accomplished using a nitrogen purge gas stream which enters the system through line 18 and is heated to a temperature of 525° F. in furnace 20 before passing through line 22 and valve 24 into bed 12. Preferably the nitrogen purge gas stream contains no more than 0.1 ppm (vol.) water, but can contain as much as 1 ppm (vol.) of water vapor. If the purge gas stream contains greater than 1 ppm (v) water, it can be introduced into the system through line 70 and passed through compressor 38, line 40, valve 42, line 44, auxilliary bed 46, line 52, valve 54 and line 56. The effluent nitrogen stream from bed 12 contains desorbed water vapor and passes through line 26, valve 28 and line 30 to condenser 32 where the temperature is reduced to about 120° F. to condense a portion of the water vapor which is removed from the system by means of knock-out or separator 34. The remaining water-containing purge gas stream can either be passed in its entirety through line 36, compressor 38, line 40, valve 42 and line 44 to auxilliary bed 46, or a portion thereof can be vented from the system through valve 48 and line 50. By passage through the auxilliary adsorption bed 46, the water content of the nitrogen purge gas stream is decreased to about 0.1 ppm (vol.) by water adsorption on the molecular sieve therein. The dry purge gas from bed 46 is then directed through line 52, valve 54 and line 56 to line 18, furnace 20 and line 22 back to primary adsorption bed 12 to complete the cycle. As required, make-up nitrogen purge gas is added to the system through line 18, or line 70, depending upon its water content. The cyclic purge desorption of bed 12 is repeated until the water loading has decreased to the desired degree, e.g., about 4 weight percent based on the dehydrated weight of the adsorbent. Thereafter the bed is cooled to 125° F. by reversing the direction of flow of the purge gas stream through bed 12. This is accomplished by closing valve 42 so that nitrogen purge gas leaving compressor 38 through line 40 is diverted through line 58, valve 60, line 30, valve 28 and line 26. In passing through the hot adsorbent in bed 12, the purge gas is heated and carries the heat energy out of the bed as the gas stream leaves through valve 24 and line 23 and then passes through line 62, valve 64, and line 52 into auxilliary bed 46. As the heated purge gas stream heats bed 46, the adsorbed water is desorbed and leaves the bed as a part of the effluent through line 44, valve 42, line 66 and valve 31. Valve 31 is used to direct the gas stream either through line 68 out of the system or through cooler 32 and knock-out 34 wherein a portion of the water content, if initially high enough, is removed from the system. The gas phase from knock-out 34 passes through line 36 and can be partially vented through valve 48 and line 50, or the entire stream passed through compressor 38, line 40, line 58, valve 60, line 30, valve 28, line 26 back to the top of primary adsorption bed 12. Make-up dry nitrogen gas as required is introduced into the system through line 70 during cooling of bed 12 and hot purge regeneration of bed 46. Any water content of the nitrogen gas stream entering bed 12 on the cyclic cool-down is deposited on the cool adsorbent at the top of bed 12 while the water-depleted purge gas stream continues through the bed with the consequent cooling of the remaining adsorbent therein. In due course bed 12 is cooled and bed 46 is regenerated and cooled. Thereafter the feedstock stream which has been passing into bed 10, is diverted to the top of bed 12 for the beginning of adsorption-purification stroke, and bed 10 is regenerated and cooled in the manner described for bed 12.

What is claimed is:

1. In the process for drying a feedstock gas stream containing at least 1 ppm (v) water vapor wherein the gas stream is passed through a first primary fixed adsorbent bed of zeolitic molecular sieves to selectively adsorb the water vapor and recover an effluent gas stream of reduced water content, periodically diverting the feedstock gas stream to a second primary fixed adsorption bed containing regenerated molecular sieve adsorbent wherein adsorptive drying of the feedstock is continued and the first primary adsorption bed is purge desorbed using a heated non-sorbable purge gas stream and thereafter cooled in preparation for having the feedstock gas stream diverted thereinto for the drying of an additional portion thereof, the improvement which comprises cyclically passing the heated non-sorbable purge gas stream through the first primary adsorption bed in a direction counter-current to the direction of flow of the feedstock gas stream therethrough and subjecting the effluent from said bed to the sequence of treatments comprising (a) decreasing the temperature of said effluent at least 75° C.;

(b) passing the cooled gas phase through an auxilliary fixed bed containing activated zeolitic molecular sieve whereby essentially all of the water vapor present therein is adsorbed; and (c) heating the effluent gas stream from said auxilliary fixed bed to the temperature desired for regeneration of the first primary fixed adsorption bed, and passing the heated gas stream into the first primary fixed bed to complete the cycle;

continuing the aforesaid cyclic purge desorption until the desired degree of bed regeneration is accomplished and thereafter cooling the first primary fixed adsorption bed and simultaneously at least partially regenerating the auxilliary fixed bed by passing a cool non-sorbable gas stream through the first primary fixed bed in a direction counter-current to the direction of cyclic flow of heated purge gas therethrough and passing at least a portion of the heated effluent therefrom through the auxilliary fixed bed, the quantity of said cool non-sorbable purge gas being sufficient to cool the first primary fixed bed to the desired temperature for a subsequent resumption of adsorption-drying of feedstock gas stream therein and sufficient to at least partially regenerate the auxilliary fixed bed.

2. Process according to claim 1 wherein the feedstock comprises ethylene, carbon dioxide and water vapor, said water vapor being present in an amount of from about 1 to 1500 ppm (v).

3. Process according to claim 2 wherein the non-sorbable purge gas is nitrogen.

4. Process according to claim 1 wherein the temperature of the effluent in step (a) is decreased at least 200° C.

* * * * *